US008289513B2

(12) United States Patent
Nelson et al.

(10) Patent No.: US 8,289,513 B2
(45) Date of Patent: Oct. 16, 2012

(54) SYSTEM AND METHOD FOR COMPONENT DISCRIMINATION ENHANCEMENT BASED ON MULTISPECTRAL ADDITION IMAGING (75) Inventors: Matthew Nelson, Harrison City, PA (US); Patrick Treado, Pittsburgh, PA (US); Charles W. Gardner, Jr., Gibsonia, PA (US)

(73) Assignee: ChemImage Corporation, Pittsburgh, PA (US)

(*) Notice: Subject to any disclaimer, the term of this patent is extended or adjusted under 35 U.S.C. 154(b) by 146 days.

(21) Appl. No.: 12/799,779

(22) Filed: Apr. 30, 2010

(65) Prior Publication Data
US 2011/0012916 A1 Jan. 20, 2011

Related U.S. Application Data (60) Provisional application No. 61/215,082, filed on May 1, 2009.

(51) Int. Cl.
G01J 3/28 (2006.01)
(52) U.S. Cl. ..................................... 356/326
(58) Field of Classification Search .............. 356/300, 356/326; 345/593
See application file for complete search history.

(56) References Cited

U.S. PATENT DOCUMENTS

| | | | |
|---|---|---|---|
| 4,749,257 A | 6/1988 | Klausz | |
| 5,080,486 A | 1/1992 | Shirasaki | |
| 5,097,352 A | 3/1992 | Takahashi | |
| 5,321,539 A | 6/1994 | Hirabayashi | |
| 5,657,121 A | 8/1997 | Nishina | |
| 5,740,288 A | 4/1998 | Pan | |
| 6,002,476 A | 12/1999 | Treado | |
| 6,014,475 A | 1/2000 | Frisken | |
| 6,262,851 B1 | 7/2001 | Marshall | |
| 6,415,077 B1 | 7/2002 | Friken | |
| 6,522,467 B1 | 2/2003 | Li | |
| 6,717,668 B2 * | 4/2004 | Treado et al. | 356/327 |
| 7,460,227 B1 * | 12/2008 | Kim et al. | 356/317 |
| 2003/0108284 A1 | 6/2003 | Danagher | |
| 2004/0109232 A1 | 6/2004 | Riza | |
| 2005/0015004 A1 * | 1/2005 | Hertel et al. | 600/425 |
| 2005/0148842 A1 | 7/2005 | Wang | |
| 2005/0228452 A1 | 10/2005 | Mourlas | |
| 2006/0119797 A1 | 6/2006 | Ockenfuss | |
| 2008/0212180 A1 | 9/2008 | Zhang | |
| 2010/0225899 A1 | 9/2010 | Treado | |

FOREIGN PATENT DOCUMENTS

WO WO2006058306 6/2006

OTHER PUBLICATIONS

Kline, Nicole J. et al., Raman Chemical Imaging of Breast Tissue, Journal of Raman Spectroscopy, vol. 28, 119-124 (1997). Levenson, Richard, "Spectral Imaging and Pathology: Seeing More," Laboratory Medicine, Apr. 2004, vol. 35, pp. 244-251.
Levenson, Richard et al, "Multiplexing with multispectral Imaging: from Mice to Microscopy," available from: http://www.cri-inc.com/assets/nuance/MultiplexingwithMSIfrommicetomicroscopy.pdf, last accessed Nov. 23, 2010.

* cited by examiner

Primary Examiner — Tarifur Chowdhury
Assistant Examiner — Abdullahi Nur (57) ABSTRACT A system and method for performing multispectral color addition imaging. An optical image is obtained for a sample scene comprising one or more target materials. Spectroscopic data is obtained for one or more target materials. A first and second waveband of interest are obtained for one or more target materials. A ratio of the first and second wavebands of interest is obtained and compared to one or more ranges of threshold values. Based on this comparison, a result is displayed wherein said result comprises a pseudo color overlay on said optical image. The pseudo color image may comprise one or more pseudo colors assigned to one or more target materials so as to differentiate and identify the target materials present in the sample scene.

16 Claims, 11 Drawing Sheets

Red Channel
630

Green Channel
635

Blue Channel
640

Color Addition
645

Figure 6B

| Colorization | Material Detected? | | | |
|---|---|---|---|---|
| | Traffic Cone | HDPE | Foam EFP | RDX NESTT |
| HDPE (Green Channel) | Yes | Yes | No | No |
| EFP (Blue Channel) | Yes | No | Yes | No |
| RDX NESTT (Red Channel) | Yes | No | Yes | Yes |
| Resultant colors from color addition | G + B + R = Brown | Green | B + R = Purple | Red |

SYSTEM AND METHOD FOR COMPONENT DISCRIMINATION ENHANCEMENT BASED ON MULTISPECTRAL ADDITION IMAGING

RELATED APPLICATIONS

This Application claims priority to U.S. Provisional Application No. 61/215,082, entitled "Method for Component Discrimination Enhancement Based on Hyperspectral Addition Imaging," filed on May 1, 2009, which is hereby incorporated by reference in its entirety. This Application is also a continuation-in-part of U.S. patent application Ser. No. 11/681,326, entitled "Polarization Independent Raman Imaging with Liquid Crystal Tunable Filter," filed on Mar. 2, 2007, which is hereby incorporated by reference in its entirety.

BACKGROUND OF THE INVENTION

There exists a need to be able to accurately detect potentially dangerous threat materials in a sample scene. Discrimination between a particular target material and a particular class of background material requires a few well-chosen wavebands. Different materials exhibit different spectral features. Therefore, a wide selection of wavelengths is necessary to address a wide variety of materials. As more types of targets and backgrounds are added to the sample scene, however, the number and location of wavelengths needed to discriminate between any given spectral pair grows rapidly.

To fully discriminate materials, spectral features must have differing intensities at different spectral locations. One possible solution would be to build many special-purpose sensors, each of which collects only a minimal set of wavebands needed for a limited set of targets and backgrounds. However, this approach has several drawbacks including cost, time, and limited results. Therefore, there exists a need for a system and method for multispectral imaging that enables cost-effective and robust results while discriminating target materials in a sample scene.

SUMMARY OF THE INVENTION

The present disclosure provides for a system and method for real time, stationary, dynamic, or on the move ("OTM") multispectral imaging. More specifically, the present disclosure provides for the use of color addition to identify target materials in a sample scene. The system and method described herein utilize a small number of spectral channels (i.e., frequencies, wavelengths, wavenumbers, energies, or colors) for rapid multispectral imaging of target materials in a sample scene. Such system and method may provide for dual wavelength imaging. The system and method described herein hold potential for accurate identification of target materials and for discriminating the chemical properties of these target materials ("analyte") from interfering background components. The system and method of the present disclosure overcome the limitations of the prior art by providing for a cost-effective and robust solution wherein one type of sensor oversamples the spectral information. The present disclosure also contemplates the use of algorithms to reduce or eliminate redundant or undesired spectral information and determining the proper number of wavelengths for analysis.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION

Reference will now be made in detail to the embodiments of the present disclosure, examples of which are illustrated in the accompanying drawings. Wherever possible, the same reference numbers will be used throughout to refer to the same or like parts.

Figure 1:
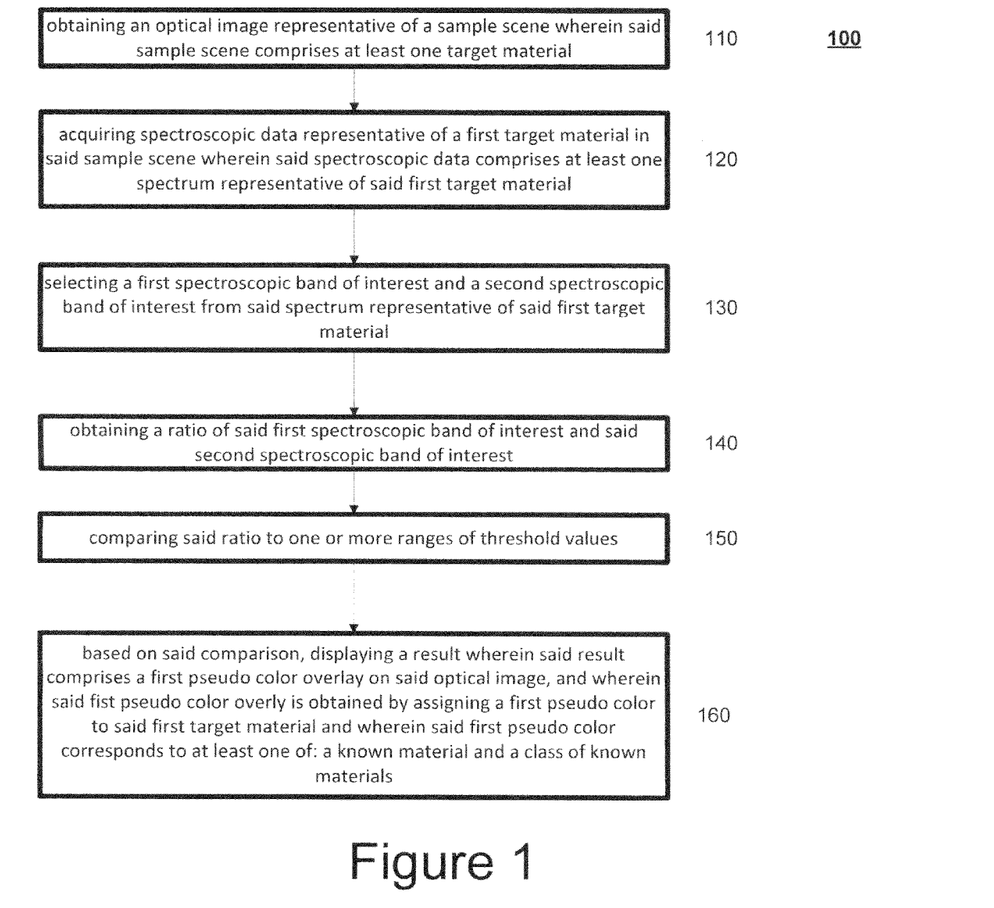
FIG. 1 is illustrative of a method of one embodiment of the present disclosure.

FIG. 1 is illustrative of a method of one embodiment of the present disclosure. The method 100 provides for obtaining an optical image representative of a sample scene wherein said sample scene comprises at least one target material in step 110. In one embodiment, said optical image may comprise a digital video image. In another embodiment, the optical image may comprise one of: a visible image, a brightfield image, an RGB image, and combinations thereof. In one embodiment, the first target material may comprise at least one of: an explosive material, a chemical material, a biological material, a hazardous material, a concealment material, and combinations thereof. In step 120, spectroscopic data representative of the first target material is acquired wherein said spectroscopic data comprises at least one spectrum representative of the first target material. In one embodiment, the spectroscopic data is selected from the group consisting of: infrared spectroscopic data, Raman spectroscopic data, fluorescence spectroscopic data, visible spectroscopic data, ultraviolet spectroscopic data, and combinations thereof. In an embodiment comprising infrared spectroscopic data, the infrared spectroscopic data may be selected from the group consisting of: short wave infrared, near infrared, mid infrared, far infrared and combinations thereof. In step 130, a first spectroscopic band of interest and a second spectroscopic band of interest are selected from said spectrum representative of the first target material. In one embodiment, one of said first spectroscopic bands of interest may comprise a band where the first target material exhibits high levels of absorption and one of said spectroscopic bands of interest may comprise a band where the first target material exhibits low levels of absorption. The present disclosure also contemplates the use of application specific algorithms or a family of algorithms that remove the redundant or undesired spectral information while preserving the information relevant to a given application. The present disclosure also contemplates the use of algorithms to assist in determining the number of wavelengths that should be used during analysis using the system and method of the present disclosure. In another embodiment, software may be used to remove the undesired or redundant spectral information and/or assist in determining the number of wavelengths that should be used.

A ratio is obtained in step 140 of said first spectroscopic band of interest and said second spectroscopic band of interest. A ratio may be obtained using any processing known in the art including but not limited to dividing the spectroscopic bands, subtracting the spectroscopic bands, and applying a chemometric technique such as partial least squares discriminate analysis ("PLSDA"). Other chemometric techniques that may be implemented include, but are not limited to, one selected from the group consisting of: principal component analysis (PCA), Cosine Correlation Analysis (CCA), Euclidian Distance Analysis (EDA), k-means clustering, multivariate curve resolution (MCR), Band T. Entropy Method (BTEM), k means clustering, Mahalanobis Distance (MD), Adaptive Subspace Detector (ASD), Spectral Mixture Resolution, and combinations thereof.

In step 150 this ratio is compared to one or more ranges of threshold values. In one embodiment, these threshold ranges may correspond to known relationships between high and low absorption spectroscopic bands of various materials that may be present in a sample scene. The present disclosure contemplates an embodiment wherein if a ratio is within a range, the target material is associated with the corresponding known material or class of materials. In other embodiments, a ratio outside of the range may be indicative of a target material not being associated with a known material or known class of materials. In yet another embodiment, whether or not a ratio is above or below a certain threshold or range of threshold values may be indicative of whether or not a target material is associated with a known material or class of materials.

Based on the comparison of a ratio with one or more ranges of threshold values, a result is displayed in step 160. In one embodiment, the result comprises a first pseudo color overly on said optical image. In one embodiment, this first pseudo color overly may be obtained by assigning a first pseudo color to said first target material and wherein said first pseudo color corresponds to at least one of: a known material and a class of known materials. In one embodiment, this methodology enables a target material in an optical image to be identifiable based on the color it is assigned. In such an embodiment, a target material can be easily identified by a user as either a threat agent (i.e., explosive, chemical hazard, biological hazard, or other hazardous agent). In another embodiment, this methodology may enable a user to identify a target material as not being a known material or belonging to known class of materials. In such an embodiment, an absence of color assigned to a target material or present in an optical image may indicate that the target material is not a threat material (i.e., not an explosive, chemical hazard, biological hazard, or other hazardous substance). It is also contemplated by the present disclosure that another embodiment may enable a user to identify a target material as a concealment material based on the presence or absence of color. The presence or absence of color can also be used in another embodiment to identify a target material as a non-threat material (i.e., plastic).

The present disclosure also contemplates the acquisition and addition of additional spectral information representative of the sample scene. In one embodiment, this additional spectral information may correspond to one or more other target materials of interest present in the sample scene. The addition of this spectral information may allow for the addition of more pseudo color information to the first pseudo color overlay (also referred to herein as "color addition"). This holds potential for improving contrast between target materials and identifying additional target materials present in a sample scene. As a result, color addition holds potential for analysis of target materials present in a sample scene and also holds potential for increasing accuracy of target material identification. This color addition therefore holds potential for reducing the number of falsely identified target materials (reducing the false alarm rate).

Figure 2:
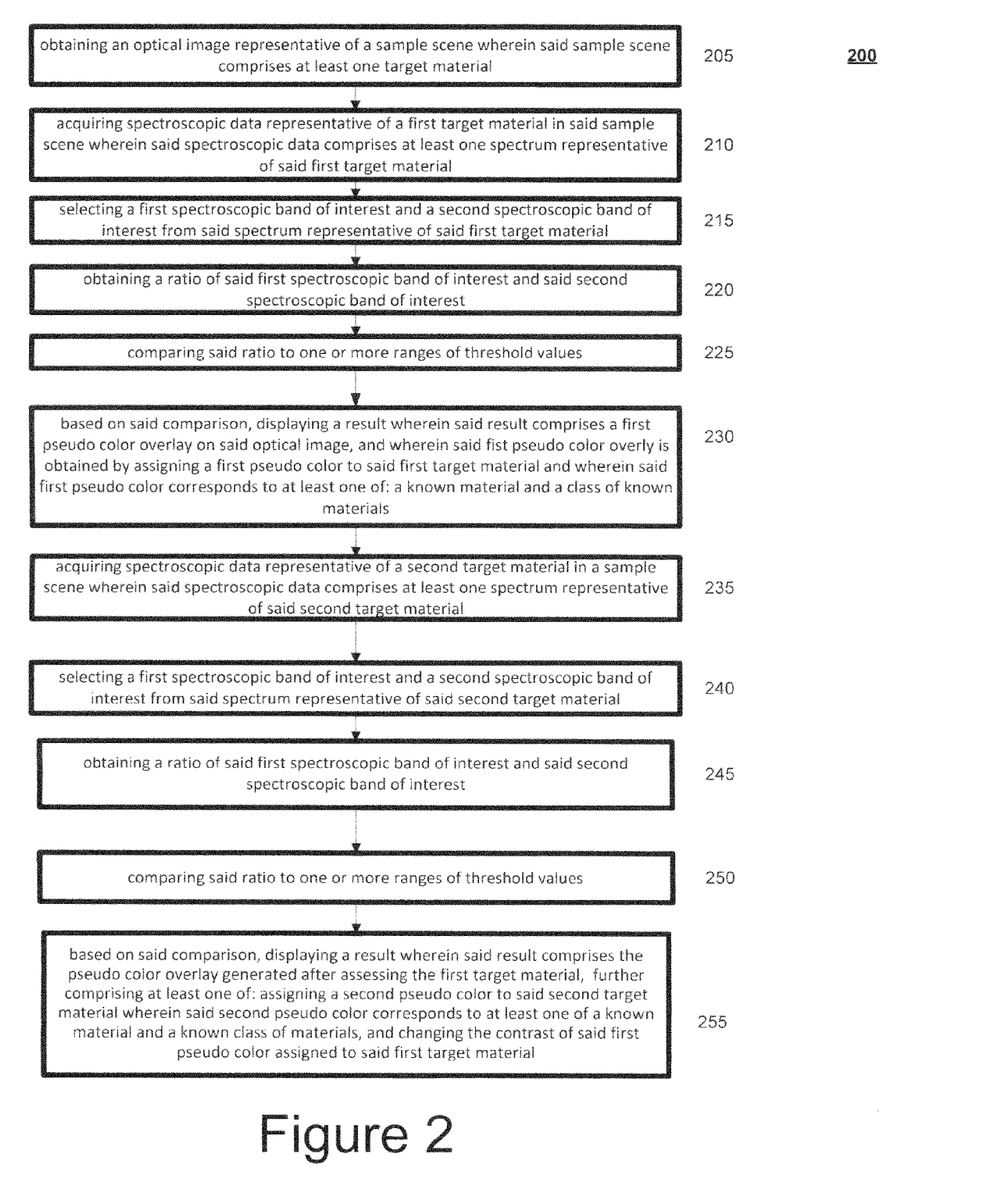
FIG. 2 is illustrative of a method of one embodiment of the present disclosure.

FIG. 2 is illustrative of a method of such an embodiment of the present disclosure. The method 200 provides for obtaining an optical image representative of a sample scene wherein said sample scene comprises at least one target material in step 205. In step 210, spectroscopic data representative of a first target material in said sample scene is obtained wherein said spectroscopic data comprises at least one spectrum representative of said first target material. In step 215, a first spectroscopic band of interest and a second spectroscopic band of interest are selected from said spectrum representative of said first target material. A ratio of said first spectroscopic band of interest and said second spectroscopic band of interest is obtained in step 220. In step 225 the ratio is compared to one or more ranges of threshold values. Based on said comparison, a result is displayed in step 230. In one embodiment, illustrated in FIG. 2, the result comprises a first pseudo color overlay on said optical image. In one embodiment, the first pseudo color overlay is obtained by assigning a first pseudo color to said first target material and wherein said first pseudo color corresponds to at least one of: a known material and a class of known materials.

In step 235 spectroscopic data representative of a second target material in the sample scene is acquired wherein the spectroscopic data comprises at least one spectrum representative of the second target material. In step 240 a first spectroscopic band of interest and a second spectroscopic band of interest from said spectrum representative of said second target material are selected. A ratio is obtained in step 245 of said first spectroscopic band of interest and said second spectroscopic band of interest. The ratio is compared to one or more ranges of threshold values in step 250. Based on said comparison, a result is displayed in step 255. In one embodiment the result comprises the first pseudo color overlay generated after assessing the first target material and further comprising at least one of: assigning a second pseudo color to said second target material wherein said second pseudo color corresponds to at least one of a known material and a known class of materials, and changing the contrast of said first pseudo color assigned to said first target material. In another embodiment, separate and distinct pseudo color overlays may be generated wherein each pseudo color overlay is assigned to a color channel. These pseudo color overlays can then be combined to obtain an image comprising all of the information contained in each individual pseudo color overlay.

In one embodiment, the spectroscopic data may be obtained by illuminating a sample to thereby generate a plurality of interacted photons wherein said photons are selected from the group consisting of: photons absorbed by the sample, photons reflected by the sample, photons scattered by the sample, photons emitted by the sample, and combinations thereof. The illumination source may comprise an active illumination source such as a laser, a passive illumination source such as the sun, and combinations thereof.

In one embodiment, the spectroscopic data may comprise infrared spectroscopic data. This infrared spectroscopic data may be data selected from the group consisting of: short wave infrared spectroscopic data, near infrared spectroscopic data, mid infrared spectroscopic data, far infrared spectroscopic data, and combinations thereof. In another embodiment, the spectroscopic data may comprise one of: Raman, fluorescence, visible, ultraviolet, and combinations thereof.

Figure 3:
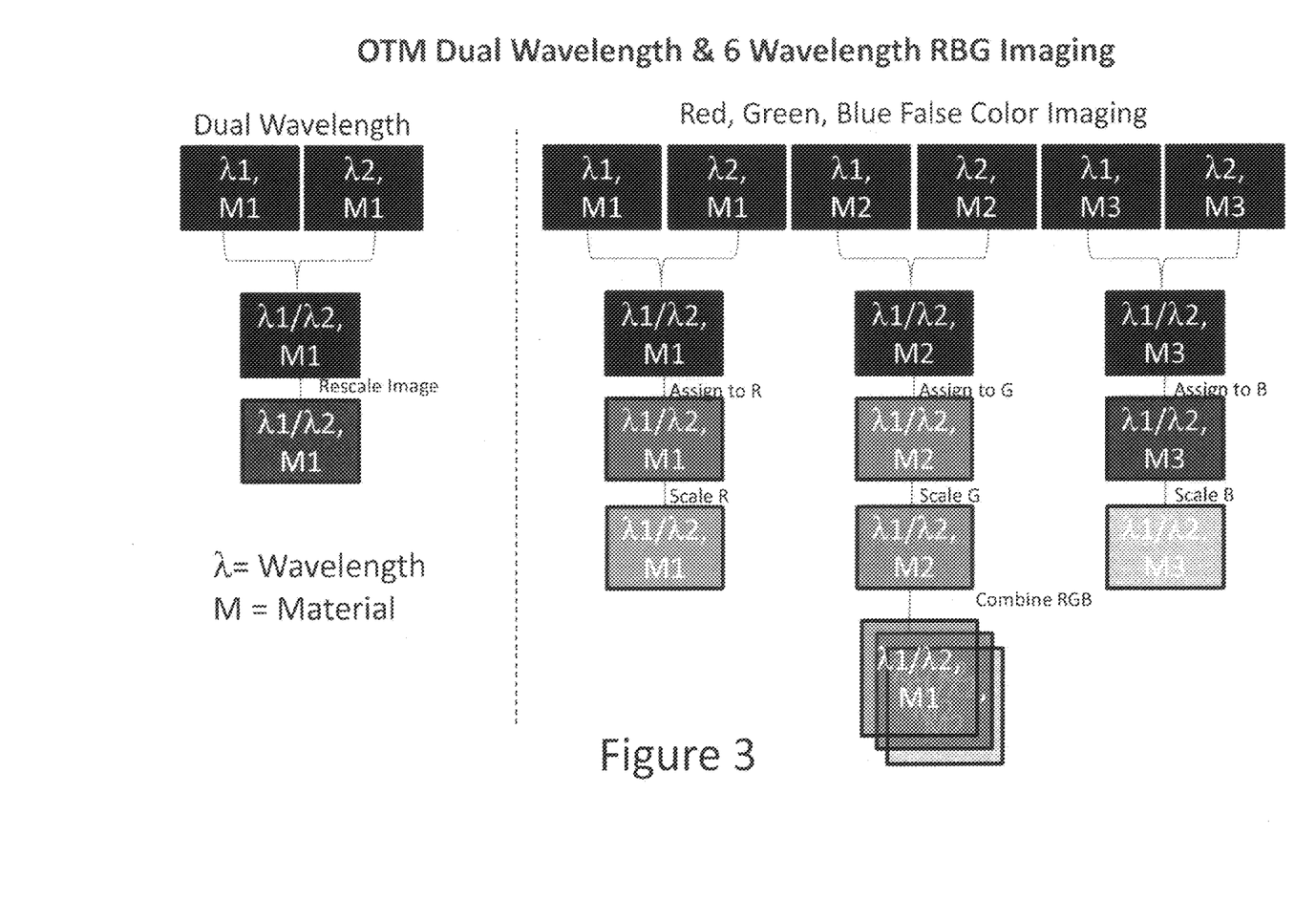
FIG. 3 is representative of an embodiment of dual wavelength imaging of the present disclosure.

FIG. 3 is a representative schematic of another embodiment of the present disclosure wherein three target materials are interrogated and the results of such analysis combined. The figure illustrates dual wavelength/RGB imaging wherein a first and second waveband for three target materials are obtained and processed (i.e., division, subtraction, chemometrics). As illustrated in the Figure, each material (M1, M2, and M3) is assigned to a color channel (red, green, and blue, respectively). These can then be combined to form a RGB false color image.

Figure 4:
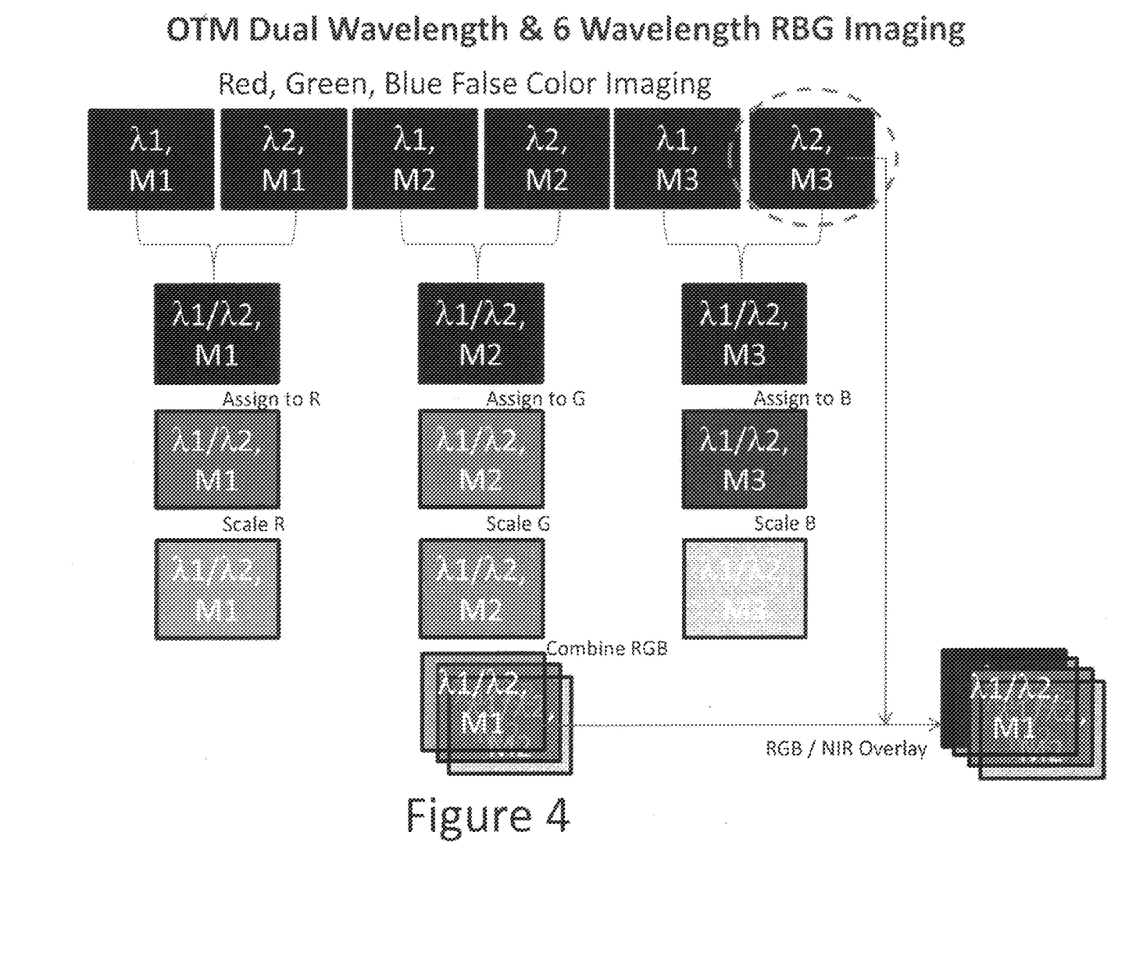
FIG. 4 is representative of an embodiment of the present disclosure combining near infrared imaging and dual wavelength imaging.

In one embodiment, the present disclosure provides for overlaying the optical image comprising a pseudo color overlay with an infrared image. The infrared image may be selected from the group consisting of: a short wave infrared image, near infrared image, mid infrared image, far infrared image, and combinations thereof. A schematic representation of the overlay of an optical image comprising pseudo (or "false color") with a near infrared image is illustrated in FIG. 4. The present disclosure also contemplates that the optical image comprising a pseudo color overlay may also be overlayed with other chemical images such as Raman, fluorescence, visible, ultraviolet, and combinations thereof.

Figure 5A:
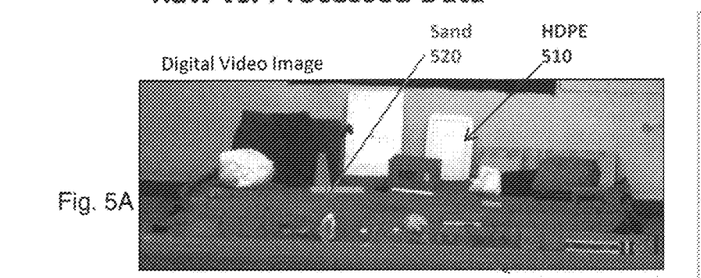
FIG. 5A is illustrative of a digital video image of a sample scene comprising at least three target materials: HDPE, sand, and AN.
Figure 5B:
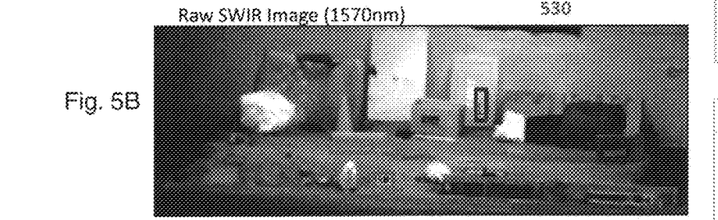
FIG. 5B is illustrative of a raw SWIR image of the sample scene of FIG. 5A with selected regions of interest 1, 2, and 3.
Figure 5C:
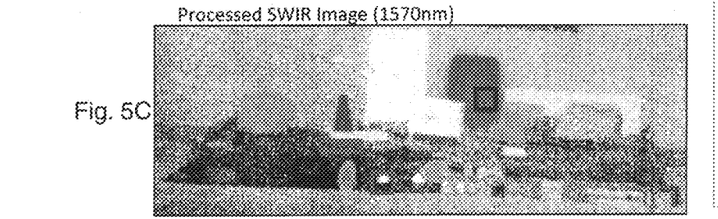
FIG. 5C is illustrative of a processed SWIR image of the sample scene of FIG. 5A and FIG. 5B with selected regions of interest 1, 2, and 3.
Figure 5D:
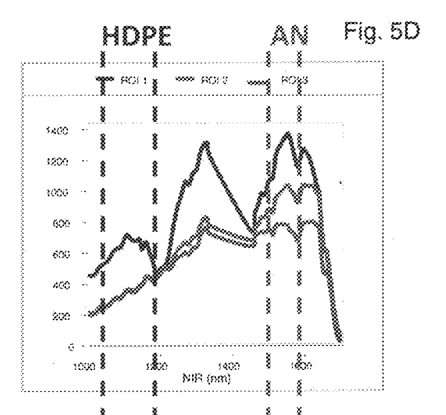
FIG. 5D is illustrative of spectra representative of the three regions of interest identified in FIGS. 5B and 5C. First and second wavebands of interest can be identified for HDPE and AN.
Figure 5E:
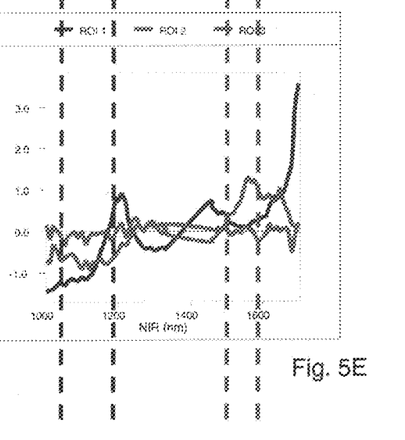
FIG. 5E is illustrative of spectra representative of the three regions of interest identified in FIGS. 5B and 5C. First and second wavebands of interest can be identified for HDPE and AN.

FIGS. 5A-5E are provided to further illustrate aspects of the embodiments of the present disclosure. A digital image of a sample scene is provided in FIG. 5A wherein the sample scene comprises various target materials. Three target materials are identified in the digital image of FIG. 5A. A first target material 510 comprises HDPE; a second target material 520 comprises sand; and a third target material 530 comprises AN. These first, second, and third target materials correspond to regions of interest ("ROI") 1, 2, and 3, respectively of the raw SWIR image in FIG. 5B and the processed SWIR image in FIG. 5C. FIGS. 5D and 5E illustrate spectral data from these three ROIs. A first spectroscopic band of interest 540 and a second spectroscopic band of interest 550 for HDPE are illustrated. Additionally, a first spectroscopic band of interest 560 and a second spectroscopic band of interest 570 for AN are illustrated.

Figure 6A:
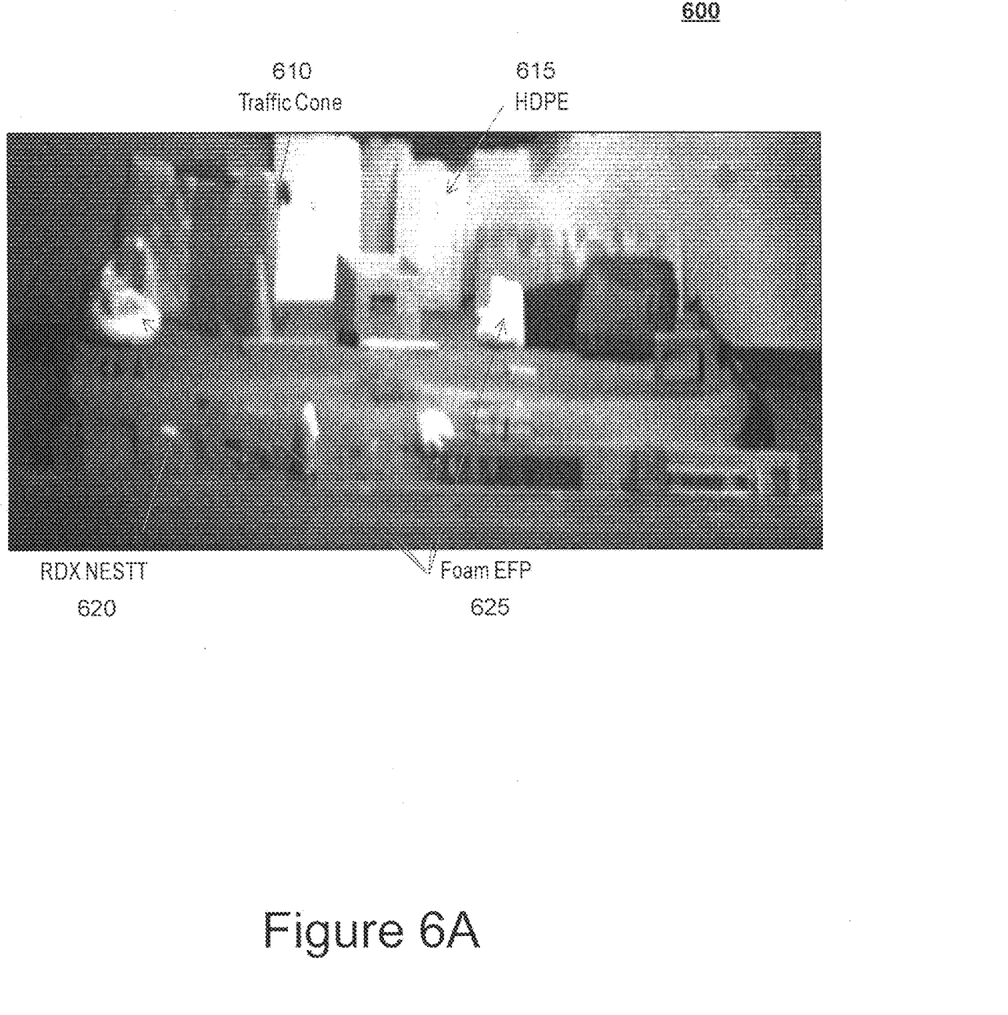
FIG. 6A is representative of an optical image of a sample scene comprising various target materials including: a traffic cone, HDPE, RDX NESTT, and foam EFP.
Figure 6B:
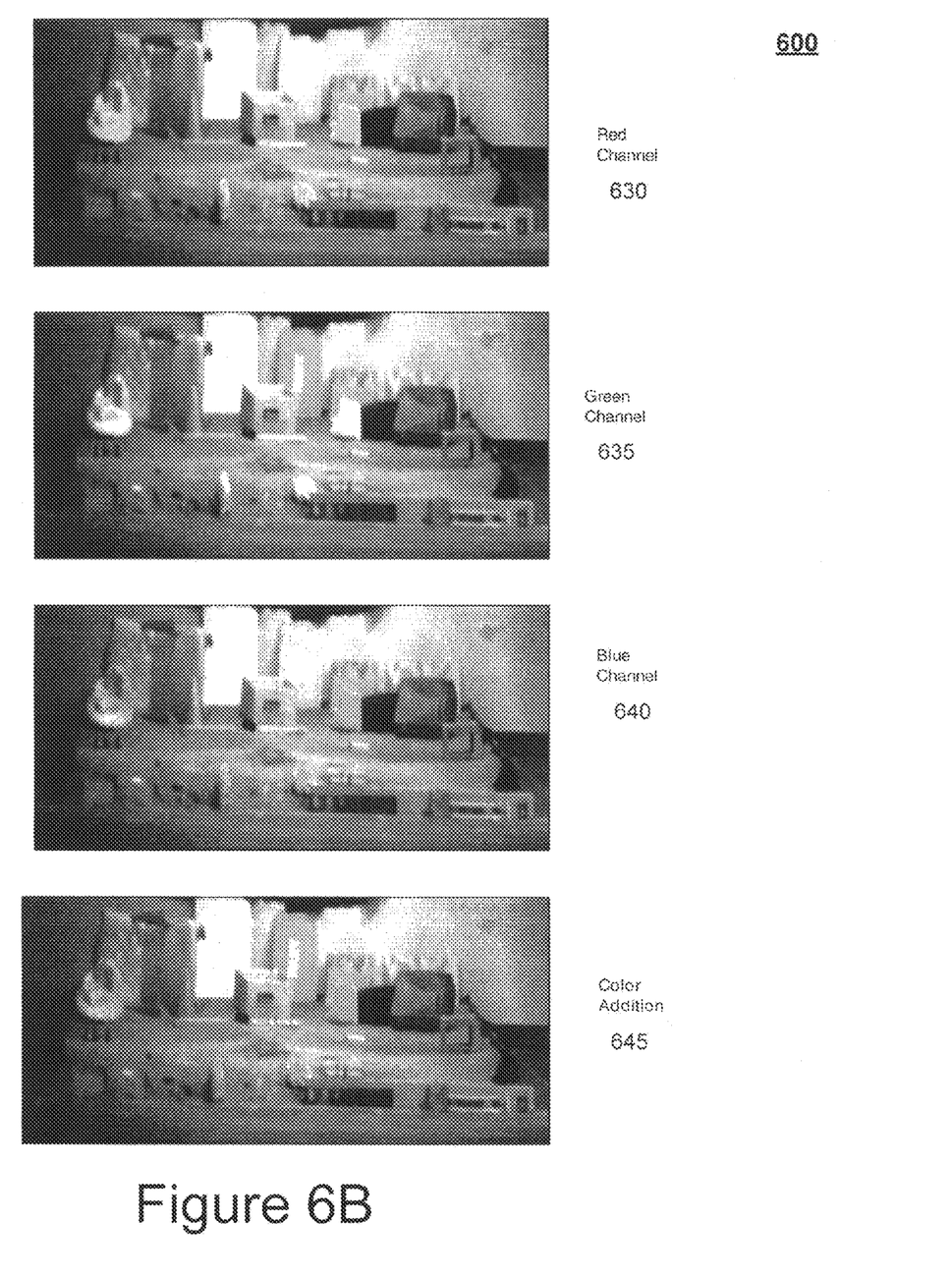
FIG. 6B is representative of the sample scene of FIG. 6A with various target materials assigned to various color channels and the resultant color addition image.
Figure 6C:
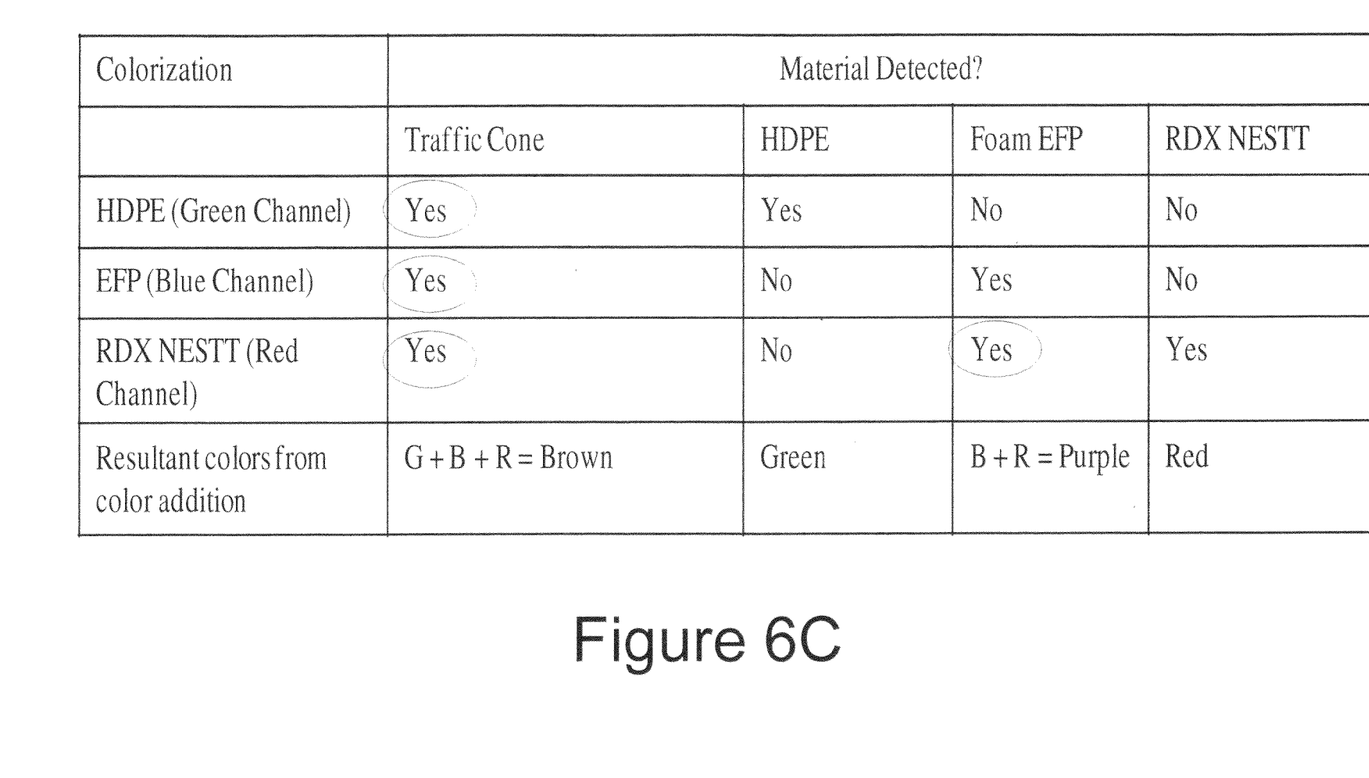
FIG. 6C is a table illustrating the reduction in false alarm rates achieved by the system and method of the present disclosure.

FIGS. 6A-6C are provided herein to further explain and exemplify embodiments of the present disclosure. FIG. 6A illustrates an optical image of a sample scene. Present in the sample scene are various target materials including: traffic cone 610, HDPE 615, RDX NESTT 620, and Foam EFP 625. FIG. 6B illustrates the colorization of these target materials for a red channel 630, a green channel 635, and a blue channel 640, respectively. FIG. 6B also illustrates color addition in 645. These figures illustrate the ability of the system and method of the present disclosure to discriminate different target materials from one another. The figure also illustrates the improvement in this discrimination after color addition is performed. Color addition provides unique, resultant colors that aid in discrimination of differing material types. FIG. 6C is a table illustrating the potential for such color addition for reducing the number of false alarms during detection. The false alarms that would have been detected if no color addition was performed are circled. As can be seen from the table, the traffic cone would have been inaccurately detected if color addition was not performed. Likewise, the foam EFP would have been inaccurately detected if color addition was not performed.

Figure 7:
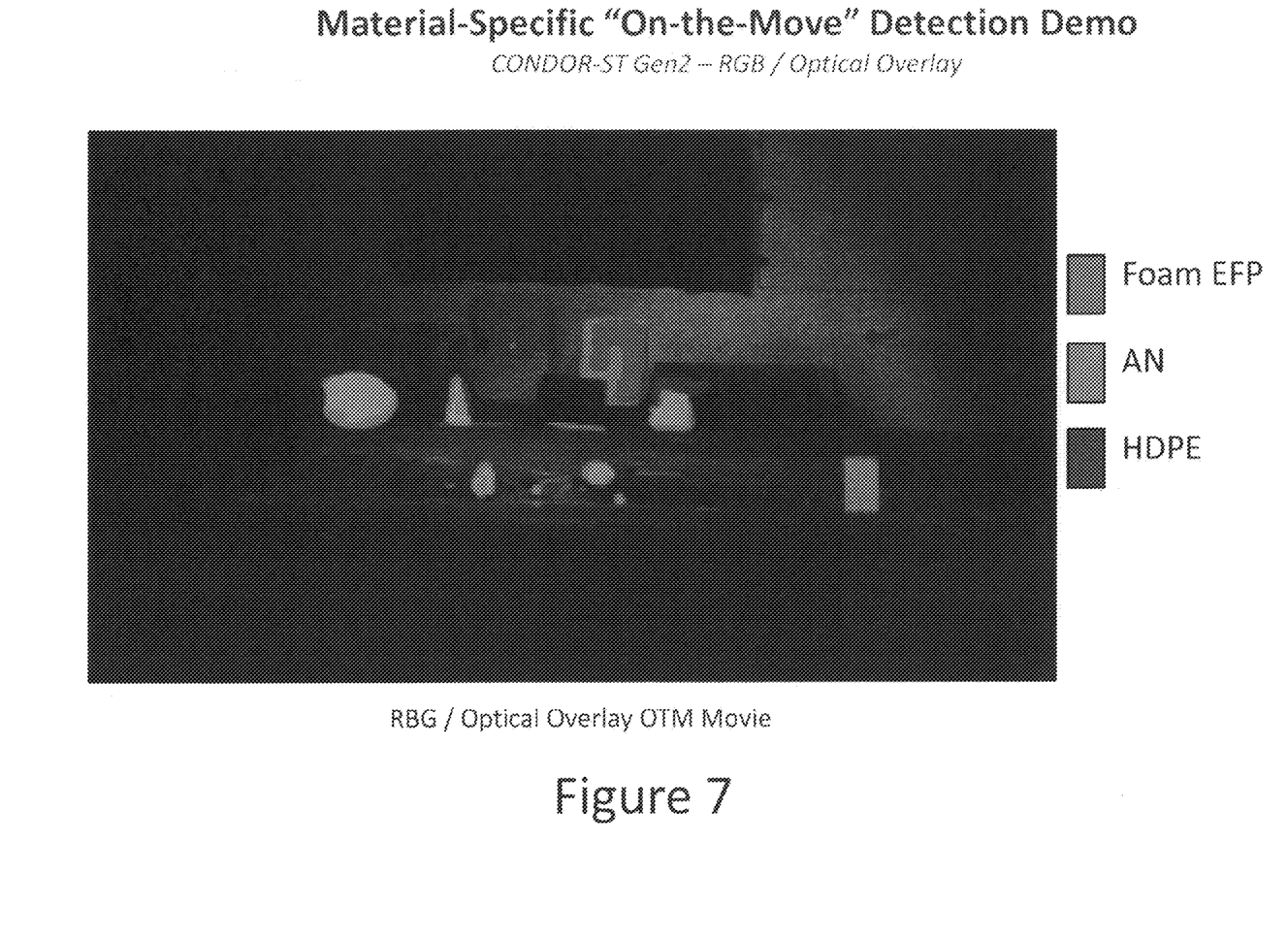
FIG. 7 illustrates OTM detection of target materials foam EFP, AN, and HDPE.

The present disclosure contemplates the use of the system and method disclosed herein in real-time, stationary, dynamic and OTM configurations. In one embodiment, the system and method of the present disclosure may be operated in a stationary mode. In another embodiment, the system and method of the present disclosure may be operated in an On-the-Move ("OTM") mode. An OTM material-specific detection result is illustrated in FIG. 7. As illustrated in FIG. 7, foam EFP, AN, and HDPE were distinguishable OTM based on their difference in color. In one embodiment, alignment techniques may be used to correct images in the OTM configuration.

The present disclosure also provides for a system for detecting target materials in a sample scene wherein images generated though two independent LCTF channels are focused side-by-side on a single CCD or independently on two CCDs. Embodiments of such a system hold potential for OTM configurations because they provide for quick (even simultaneous) imaging and may eliminate the need for aligning images. However, the present disclosure also contemplates the use of these embodiments in other configurations including stationary imaging.

In one embodiment, the present disclosure may incorporate technology available from ChemImage Corporation, Pittsburgh, Pa. including that described more fully in U.S. Pat. No. 7,69,2775, filed on Jun. 9, 2006, entitled "Time and Space Resolved Standoff Hyperspectral IED Explosives LIDAR Detection", U.S. patent application Ser. No. 12/199, 145, filed on Aug. 27, 2008, entitled "Time Time and Space Resolved Standoff Hyperspectral IED Explosives LIDAR Detector," U.S. Pat. No. 7,692,776, filed on Dec. 22, 2006, entitled "Chemical Imaging Explosives (CHIMED) Optical Sensor,"and U.S. application patent Ser. No. 12/754,229, filed on Apr. 5, 2010, entitled "Chemical Imaging Explosives (CHIMED) Optical Sensor Using SWIR." These patents and applications are hereby incorporated by reference in their entireties.

Figure 8A:
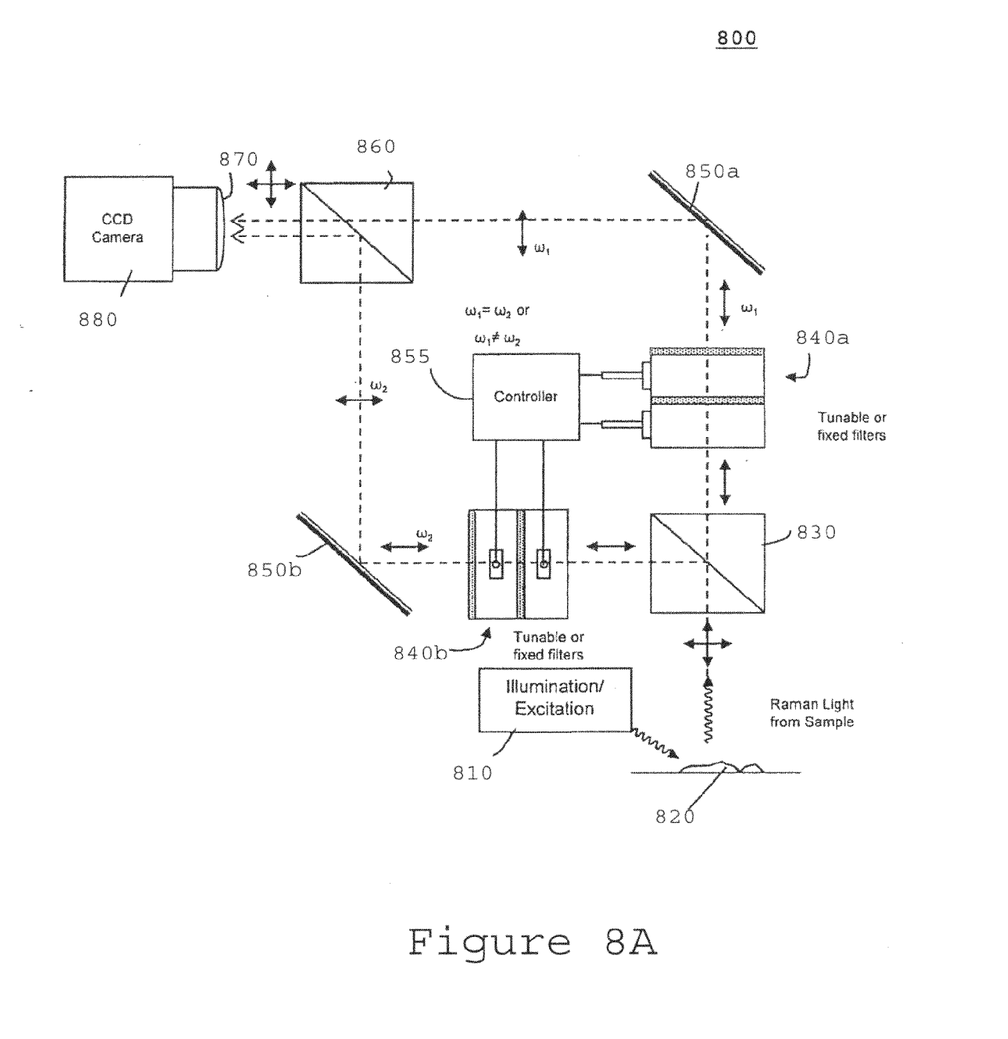
FIG. 8A is a schematic representation of an embodiment of a system of the present disclosure.
Figure 8B:
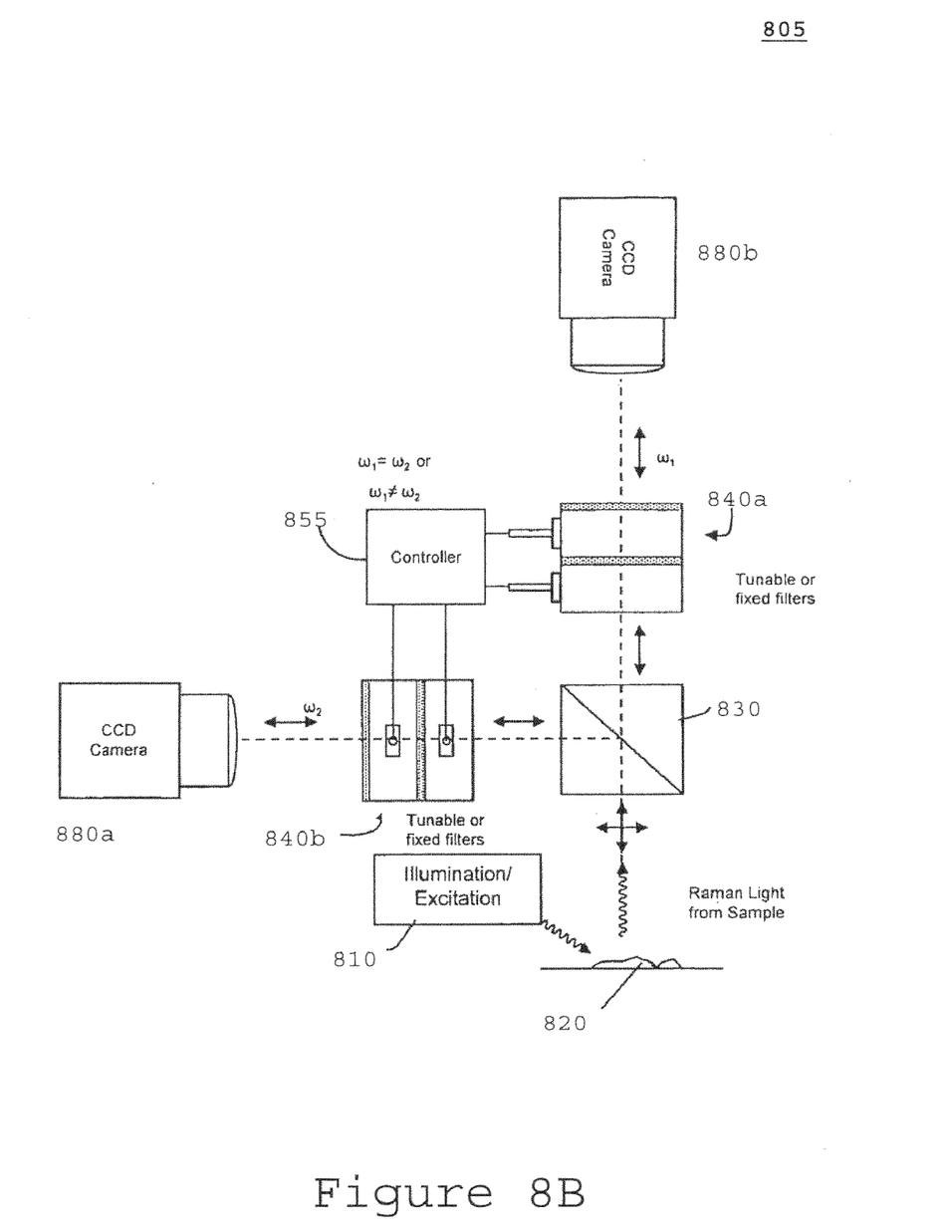
FIG. 8B is a schematic representation of an embodiment of a system of the present disclosure.

FIGS. 8A and 8B are schematic representations of embodiments of a system of the present disclosure comprising more than one filter wherein said filters comprise at least one of: a tunable filter, a fixed filter, and combinations thereof, along distinct orthogonal beam paths. In one embodiment, the system may comprise at least one tunable filter selected from the group consisting of: a multi-conjugate tunable filter, a liquid crystal tunable filter, an electro-optical tunable filter, an acousto-optical tunable filter, and combinations thereof. In one embodiment, the system may comprise multi-conjugate tunable filter technology available from ChemImage Corporation, Pittsburgh, Pa. Multi-conjugate tunable filter technology is more fully described in U.S. Pat. No. 7,362,489, filed on Apr. 22, 2005, entitled "Multi-Conjugate Liquid Crystal Tunable Filter" and U.S. Pat. No. 6,992,809, filed on Feb. 2, 2005, also entitled "Multi-Conjugate Liquid Crystal Tunable Filter."

The choice of tunable filter depends on the desired optical region and/or the nature of the sample being analyzed. In another embodiment, the tunable filter may comprise a filter selected from the group consisting of: a Fabry Perot angle tuned filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter. In one embodiment, the tunable filer may be selected to operate in one or more of the following spectral ranges: the ultraviolet (UV), visible, near infrared, and mid-infrared.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, telescopes are appropriate image gathering optics.

In the arrangement of FIG. 8A, an illumination or excitation source 810 is provided to illuminate a target material 810 (or "sample") to thereby produce interacted photons. These interacted photons enter a polarization cube 830 wherein the interacted photons are split into two independent beam paths. These two independent beam paths are passed through independent tunable or fixed filters 840a and 840b. The paths of the filtered beams are not parallel through the filters 840a and 840b. They are directed to a element 860 which may comprise a polarizing cube, a polarizing beam splitter, or a beam combiner via appropriate reflectors (i.e., mirrors) 850a and 850b. At element 860 the orthogonal components, which can be at the same or different passband wavelengths $\omega_1$ and $\omega_2$, are directed to a CCD sensor 880 through a lens assembly 870 such that they are not recombined but rather focused side-by-side on the CCD sensor 880. In one embodiment, a switching mechanism (not shown) may be provided to switch between the two views (or spectral images) corresponding to the spectral data collected by the CCD sensor 880 from each of the filters 840a and 840b.

The system may further comprise a controller 855 may be configured to tune the filters 840a and 840b. In one embodiment, the controller 855 may be controlled by a computer (not shown) that may also carry the interface elements coupled to and controlling the CCD 880 and contain a display on which the collected image can be viewed, stored, transmitted over a network, etc. The controller 855 may also be used to tune the filters 840a and 840b in unison. In another embodiment, the controller 855 may independently tune the passband wavelengths $\omega_1$ and $\omega_2$ that respectively process components of the input. Therefore, by appropriate control, the filters 840a and 840b can be tuned to the same wavelength or to two different passband wavelengths ($\omega_1 \neq \omega_2$) at the same time. The controller 855 may be programmable or implemented in software to allow a user to selectively tune each filter 840a and 840b as desired.

FIG. 8B is a schematic representation of another embodiment of a system of the present disclosure. In this embodiment, the beam combiner 860 may be removed and two CCD cameras may be used, 880a and 880b. In one embodiment, each CCD camera may be optically coupled to a corresponding one of the two filters 840a and 840b to capture filtered signals from the filter and to responsively generate electronic signals that enable display of spectral images of the illuminated sample 820.

It is noted here that although laser light may be coherent, the light received from the sample 820 (e.g., visible light, Raman scatter, fluoresce emission, infrared absorbance or reflectance) and fed to the filters 840a and 840b may not be coherent. Therefore, wavefront errors may not be present or may be substantially avoided in the two filter versions of FIGS. 8 and 9 because of processing of non-coherent light by each filter 840a and 840b.

The present disclosure may be embodied in other specific forms without departing from the spirit or essential attributes of the disclosure. Although the foregoing description is directed to the embodiments of het disclosure, it is noted that other variations and modifications will be apparent to those skilled in the art, and may be made without departing from the spirit of scope of the disclosure.

What is claimed is:

1. A method comprising:
obtaining an optical image representative of a sample scene wherein said sample scene comprises at least one target material;
acquiring spectroscopic data representative of a first target material in said sample scene wherein said spectroscopic data comprises at least one spectrum representative of said first target material;
selecting a first spectroscopic band of interest and a second spectroscopic band of interest from said spectrum representative of said first target material;
obtaining a ratio of said first spectroscopic band of interest and said second spectroscopic band of interest;
comparing said ratio to a range of threshold values; and
based on said comparison, displaying a result wherein said result comprises a first pseudo color overlay on said optical image, and wherein said first pseudo color overly is obtained by assigning a first pseudo color to said first target material and wherein said first pseudo color corresponds to at least one of: a known material and a class of known materials.

2. The method of claim 1 wherein said spectroscopic data comprises infrared spectroscopic data.

3. The method of claim 2 wherein said infrared spectroscopic data comprises spectroscopic data selected from the group consisting of: short wave infrared spectroscopic data, near infrared spectroscopic data, mid infrared spectroscopic data, far infrared spectroscopic data, and combinations thereof.

4. The method of claim 1 wherein said first target material is a material selected from the group consisting of: an explosive material, a chemical material, a biological material, a hazardous material, a concealment material, and combinations thereof.

5. The method of claim 1 further comprising overlaying said result with an infrared image.

6. The method of claim 5 wherein said infrared image is an image selected from the group consisting of: a short wave infrared image, near infrared image, mid infrared image, far infrared image, and combinations thereof.

7. The method of claim 1 wherein said optical image comprises a digital video image.

8. The method of claim 1 wherein said method is performed in at least one of the following modes: an on the move mode, a stationary mode, and combinations thereof.

9. The method of claim 1 further comprising:
acquiring spectroscopic data representative of a second target material in a sample scene wherein said spectroscopic data comprises at least one spectrum representative of said second target material;

selecting a first spectroscopic band of interest and a second spectroscopic band of interest from said spectrum representative of said second target material;

obtaining a ratio of said first spectroscopic band of interest and said second spectroscopic band of interest;

comparing said ratio to a range of threshold values; and based on said comparison, displaying a result wherein said result comprises the pseudo color overlay of claim 1 further comprising at least one of:

assigning a second pseudo color to said second target material wherein said second pseudo color corresponds to at least one of a known material and a known class of materials, and changing the contrast of said first pseudo color assigned to said first target material.

10. The method of claim 9 wherein said spectroscopic data comprises infrared spectroscopic data.

11. The method of claim 10 wherein said infrared spectroscopic data comprises spectroscopic data selected from the group consisting of: short wave infrared spectroscopic data, near infrared spectroscopic data, mid infrared spectroscopic data, far infrared spectroscopic data, and combinations thereof.

12. The method of claim 9 wherein said second target material is a material selected from the group consisting of: an explosive material, a chemical material, a biological material, a hazardous material, a concealment material, and combinations thereof.

13. The method of claim 9 further comprising overlaying said result with an infrared image.

14. The method of claim 13 wherein said infrared image is an image selected from the group consisting of: a short wave infrared image, near infrared image, mid infrared image, far infrared image, and combinations thereof.

15. The method of claim 9 wherein said optical image comprises a digital video image.

16. The method of claim 9 wherein said method is performed in at least one of the following modes: an on the move mode, a stationary mode, and combinations thereof.

* * * * *